United States Patent [19]

Dattagupta et al.

[11] Patent Number: 4,734,363
[45] Date of Patent: Mar. 29, 1988

[54] LARGE SCALE PRODUCTION OF DNA PROBES

[75] Inventors: Nanibhushan Dattagupta, New Haven; Peter M. M. Rae, Hamden; Donald M. Crothers, Northford; Thomas R. Barnett, East Haven, all of Conn.

[73] Assignee: Molecular Diagnostics, Inc., West Haven, Conn.

[21] Appl. No.: 675,386

[22] Filed: Nov. 27, 1984

[51] Int. Cl.$^4$ .......................... C12P 19/34; C12Q 1/68
[52] U.S. Cl. .......................................... 435/91; 435/6; 935/2; 935/78; 536/27
[58] Field of Search ................... 436/501, 504; 435/6, 435/91, 172.1; 935/2, 76, 78; 536/27-29

[56] References Cited

U.S. PATENT DOCUMENTS

| | | | |
|---|---|---|---|
| 4,139,346 | 2/1979 | Rabbani | 436/504 |
| 4,302,204 | 11/1981 | Wahl | 436/501 |
| 4,486,539 | 12/1984 | Ranki | 436/504 |
| 4,542,102 | 9/1985 | Dattagupta | 435/6 |
| 4,563,419 | 1/1986 | Ranki | 435/6 |

OTHER PUBLICATIONS

Ashley, P. L. et al, Analytical Biochemistry, 140(1): 95–103 (1984), cited in Chem. Abst., CA 101(7): 509846y.
*Microbiology*, B. D. Davis et al, eds., Harper & Row, pub., Philadelphia (1980), pp. 171–178 and 207–210.

*Primary Examiner*—Margaret Moskowitz
*Attorney, Agent, or Firm*—Sprung Horn Kramer & Woods

[57] ABSTRACT

A process for production of a single strand of a nucleic acid comprising covalently linking to a solid substrate a polynucleotide complementary to the desired strand, hybridizing said polynucleotide with an oligonucleotide, extending the oligonucleotide in direction away from said substrate, denaturing the hybridized polynucleotide and extended oligonucleotide, thereby to free the extended oligonucleotide from the solid substrate, and separating the extended oligonucleotide. The product can be used for making analytical probes.

9 Claims, 1 Drawing Figure

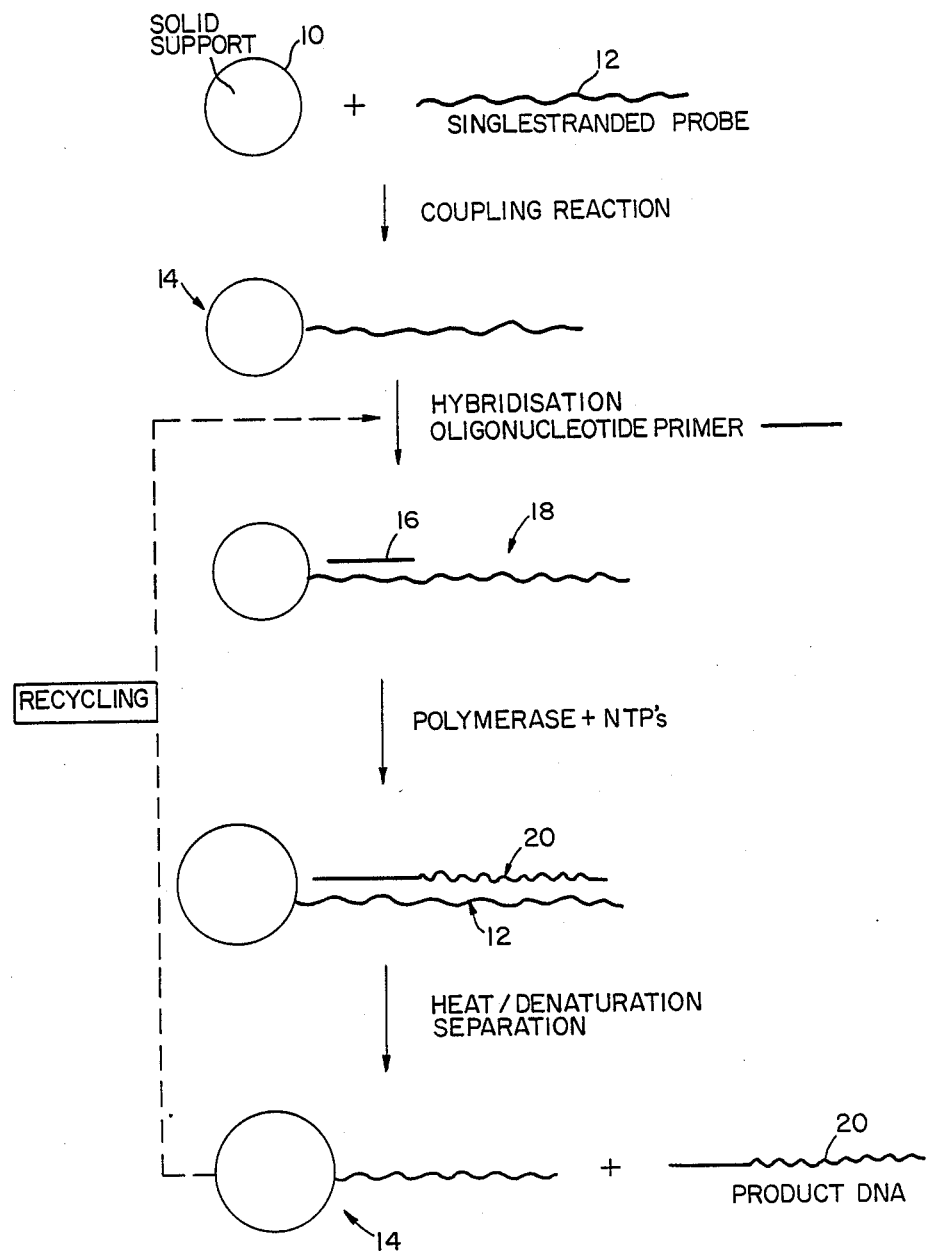

LARGE SCALE PRODUCTION OF DNA PROBES

BACKGROUND OF THE INVENTION

1. Field of the Invention

This invention relates to a method for the large scale production of a specific nucleic acid sequence:

2. Background Information

Large scale production of a nucleic acid sequence is usually done by cloning the particular sequence in a specific vector. The sequence to be cloned is isolated, identified and then coupled covalently to a single or double-stranded vector. The vectors with the extra DNA are separated from the host cell and, depending on the requirements, the cloned piece of DNA has to be restricted and separated from the rest of the DNA. If one requires single-stranded DNA, either it is cloned in a single-stranded vector or strand separator is necessary. All these techniques involve skilled manipulation of biochemical and biological systems.

Analytical Biochemistry, 140, 95-103(1984) describes a method of producing DNA hybridization probes by non-specifically immobilizing single strand DNA template to cellulose. Although the method is useful, the length distribution of the newly synthesized product DNA is not as uniform as might be desired. It now appears this may be due to multiple attachments of the template DNA to the cellulose.

SUMMARY OF THE INVENTION

It is accordingly an object of this invention to synthesize specific nucleic acid sequences on a relatively large scale without the continual need for plasmids, cloning and restriction.

This and other objects and advantages are realized in accordance with the present invention pursuant to which there is provided a process for production of a single strand of nucleic acid comprising covalently linking to a solid substrate a polynucleotide complementary to the desired strand, hybridizing said polynucleotide with an oligonucleotide, extending the oligonucleotide in direction away from said substrate, denaturing the hybridized polynucleotide and extended oligonucleotide, thereby to free the extended oligonucleotide from the solid substrate, and separating the extended oligonucleotide from the solid support carrying the covalently linked polynucleotide which support is then recycled to an earlier step in the process.

The intermediate product comprising a solid substrate, a single-stranded polynucleotide covalently linked to the solid substrate, and an oligonucleotide hydridized to the polynucleotide is also new.

BRIEF DESCRIPTION OF THE DRAWING

The drawing is a schematic diagram depicting the formation of a structure according to the present invention.

DETAILED DESCRIPTION OF THE INVENTION

The invention will be further described with reference to the accompanying drawing which is a flow sheet of a preferred process.

A solid support 10 is covalently coupled to a DNA strand 12 complementary to the desired strand to be synthesized, the DNA strand having its 3'-end adjacent to the solid support. This product, 14, is known.

An oligonucleotide 16 corresponding to the 5'-end of the desired strand is then hybridized to strand 12 of product 14. This solid new intermediate 18 is contacted with a solution containing nucleoside triphosphates and the Klenow fragment of DNA polymerase, whereupon the oligonucleotide grows at its 3'-end, following the DNA strand 12 serving as a template, producing the desired strand 20 base-paired to 12. The structure constituting the polynucleotide base-paired to the extended oligonucleotide is denatured so as to release the strand 20 to the solution and then the strand-containing solution is separated from the product 14, as by centrifugation, the product 14 then being recycled to an earlier step in the process.

The desired strand 20 can be recovered from its solution in any known manner.

Describing the invention in greater detail, the solid support can be cellulose, Sephadex, or Sepharose, a piece of paper, nylon or anything which can be used to react with an amine or aldehyde or similar residue.

The nucleic acid is linked to the solid support in a known manner, e.g., the latter providing an aldehyde or amine reactive group which can react with an amine or aldehyde group provided on the nucleic acid to form a Schiff's base, followed by its reduction as with a borohydride to form an aminomethylene joinder between support and nucleic acid. This is described more fully in application Ser. No. 582,503, filed Feb. 22, 1984, now pending. The link can also be a phosphate ester, etc.

After the gene probe or the gene to be copied has been immobilized, it is primed with a suitable piece of oligonucleotide such that the 5' end of the oligonucleotide will hybridize to the 3' end of the immobilized DNA. Since the 3' end of the immobilized DNA is closer to the solid support, the 5' end of the oligonucleotide will also be closer to the solid support and the 3' hydroxyl residue of the oligonucleotide primer will be available for primer extension by several DNA synthesis enzymes, for example, DNA polymerase, Klenow fragment of DNA polymerase or reverse transcriptase. After the primer has been hybridized to the immobilized DNA, it can be extended by using those enzymes and suitable nucleoside triphosphate substrates. After the enzyme reaction is over, and the enzyme is washed away, one can separate the newly synthesized DNA strand by heating the solution or by adding some denaturing agent, for example, sodium hydroxide solution, formamide or dimethyl sulfoxide.

The solid support carrying immobilized nucleic acid is separated from the solution containing the desired strand as by filtration and/or centrifugation and the solid support can be recycled, if desired, after washing.

the supernatant containing the desired strand is subjected to dialysis, alcohol precipitation or the like, to obtain pure strand which can then be used in known manner. One such use if for making probes for diagnostic tests.

The invention will be further described in the following illustrative examples wherein all parts are by weight unless otherwise expressed or apparent from the context.

EXAMPLE 1

Site Specific Immobilization of the DNA for the purpose of large scale production of the DNA probes for sickle cell anemia diagnosis.

A segment of β-globin gene containing 737 nucleotide residues has been cloned in a vector M13mp7. Since the cloning sites on M13mp7 are in an inverted repeat, they exist in a double-stranded form even in single stranded M13 DNA. This double-stranded site can be digested with proper restriction enzyme. M13mp7 vector with ~740 residues of β-globin inserted is first digested with the restriction enzyme which is either BamH1 or EcoR1. The strands are then separated by gel electrophoresis. The fragment containing the globin insert is immobilized onto Sephadex G25 by the following procedure:

First the Sephadex particular is activated with CNBr as has been described in Example 2. The 737 globin insert-containing fragment is tailed with terminal deoxynucleotidyl transferase using ATP as a substrate (Examples 3 and 4). ATP, being a ribonucleoside triphosphate, contains a sugar residue which can be oxidized to produce a dialdehyde. These dialdehyde residues can then be reacted with the amide on the solid support to form a Schiff base which can be reduced to produce secondary amine linkage between the solid support and the DNA.

After the probe is immobilized, a primer containing 19 nucleotides is hybridized with the immobilized DNA and then the primer extension is performed by using either Klenow fragment of DNA polymerase 1 or reverse transcriptase as will now be described.

EXAMPLE 2

Preparation of the solid support containing Amine ($NH_2$) groups

Sephadex G25 powder (0.5 g) is mixed with 5 ml distilled water at room temperature for approximately 30 minutes. The product is washed with distilled water and resuspended in 20 ml ice cold distilled water. The suspension is adjusted to pH 10.5–11 with a 5M solution of sodium hydroxide. The suspension is cooled in an ice-bath (4° C.) and 1.0 g solid cyanogen bromide is added to the suspension. The suspension is retained in the ice-bath and continuously stirred for 30 minutes. During this period, the pH is continuously monitored and maintained at 10.5–11 with sodium hydroxide (5M). The suspension is washed with ice cold distilled water and treated wit approximately 5 ml of hexamethylene diamine (1M solution in $H_2O$, adjusted to pH 9–10 with HCl). The Sephadex amine product is washed with water or other suitable buffer, depending on the future use of the product.

EXAMPLE 3

Terminal Transferase Addition of Ribonucleotides

A ribonucleotide or deoxyribonucleotide can be coupled to the 3'-hydroxyl terminus of a DNA molecule or oligonucleotide by the enzymatic action of terminal deoxynucleotidyl transferase. Twenty (20) μl DNA 737 bp approximately $5 \times 10^{-13}$ moles are dissolved in 20 μl potassium cacodylate (1M, pH 7.2). This solution is incubated with 40 μl distilled water, 5–20 μl dithio threitol (DTT) (2 mM), 1–2 μl ribonucleoside triphosphate (10 mM) and 50 μl magnesium chloride (20 mM) at 37° C. for 5 minutes. The reaction mixture is subsequently cooled in an ice-bath for 10 minutes. Terminal deoxynucleotidyl transferase (14–20 units) is added and the mixture is incubated at 15° for 24 hours. The modified nucleic acid can be isolated from non-coupled nucleotides and protein by phenol extraction and alcohol precipitation.

EXAMPLE 4

Coupling of End Labeled Nucleic Acids to a Solid Support (a) Coupling via Schiff's base formation.

It is known that cis-diols can be oxidized by periodate to form dialdehydes. The dialdehydes can form Schiff's base with a primary amine group via the addition of —$NH_2$. The Schiff's base can be reduced with sodium borohydride to form a secondary amine.

In a similar manner, (DNA containing a ribonucleotide at the 3'-hydroxyl terminus (Example 3) is dissolved in sodium acetate buffer, 0.1M, pH 5 at a concentration of 1 mM. Twenty (20) μl of sodium metaperiodate (100 mM) is added to 1 ml of the nucleic acid solution. The reaction is allowed to proceed for 40 minutes at room temperature (25° C.). Following the reaction, the pH is adjusted to 8 with sodium hydroxide solution. The solution is added to a Sephadex-amine (Example 2), prepared as described above, suspended in a suitable buffer suc as 0.1M sodium acetate pH 8. The reaction is allowed to proceed for 30 minutes at room temperature (25° C.) resulting in the formation of a suspension of Schiff's base. The Schiff's base is reduced by the addition of sodium borohydride. The reduction is carried out in four steps: Approximately 0.15 ml of freshly prepared sodium borohydride solution (200 mM) is added and the reaction is allowed to proceed for 30 minutes. Approximately 0.15 ml of sodium borohydride solution is again added to the reaction mixture and the reaction is continued for 60 minutes. Another 0.15 ml of the sodium borohydride in subsequently added to the reaction mixture. After 90 minutes, another aliquot of 0.15 ml of the soidum borohydride solution is added to complete the reaction. The suspension is contrifuged for 30 minutes at 2000 g. The supernatant is decanted and the wash is repeated 3 times. The pellet is resuspended in 5 ml of the hybridization buffer as in Example 5.

EXAMPLE 5

Hybridization of the Oligonucleotide 19A' with the Immobilized 737 Insert as in Example 4

The 737 insert immobilized support is suspended in a buffer containing 50 mM tris and 1 mM dithiothreitol. Oligonucleotide 19A', Proc. Natl. Acad. Sci. USA 80, 278 (1983) is dissolved in the same buffer and is added to the suspension. The whole mixture is heated to 65° C. and then brought down slowly to 50° C. The mixture is left for 15 minutes after which time it is cooled to room temperature. Unreacted, unhybridized oligonucleotide is removed by wasing at 0° C. with the same buffer. The hybrid containing the immobilized support DNA is washed with 50 mM tris buffer, pH 7.2.

EXAMPLE 6

The Preparation of the Hybridization Probe using Reverse Transcriptase of the Klenow Fragment of DNA Polymerase 1

The hybrid immobilized onto the solid support produced in Example 2 is taken in a buffer containing 50 mM tris, pH 7.2, 10 mM magnesium sulfate, 1 mM dithiothreitol, 50 micrograms per ml BSA and 200 nM each of deoxy ATP, deoxy CTP, deoxy GTP, deoxy TTP and, e.g., 5 units reverse transcriptase or Klenow fragment of DNA polymerase. The whole mixture is incubted at room temperature for 30 minutes and the reaction is stopped by centrifuging the supernatant and removing the solid particles. The solid particles are washed with the same buffer and heated to 40° C. after adding 80% formamide to remove the newly synthesized probe from the solid support. The support is washed thoroughly with water, then with tris buffer and it is recycled as in Example 2 and 3. The synthesized probe is then analyzed by gel electrophoresis to determine the length.

EXAMPLE 7

Cloning of a Beta-Globin Gene Segment in M13

To prepare a single-stranded segment of the beta-hemoglobin gene that can be separated from the phage DNA in which it is propagated, an approximately 740 base pair Alu I segment of the globin gene was inserted into the linker region of the double stranded replicative form of M13mp7.

The linker region that has been incorporated into the phage DNA is not only rich in restriction enzyme cleavage sites, but is a reverse repeat, and has the priority of forming a duplex in otherwise single-stranded phage DNA. Restriction enzymes require double-stranded DNA as a substrate; thus the mp7 phage DNA can be cleaved by the enzyme. Cloning of a foreign DNA segment into the Hinc II site, for example, allows digestion of the single-stranded phage DNA by such enzymes as EcoRI or Bam HI, separating the recombinant phage DNA into vector and insert strands that are readily separable from one another.

The 740 bp Alu I segment of the beta-globin gene comprises the beginning of the gene and a portion of its upstream flank. The segment was initially cloned by converting the Alu I ends to EcoRI ends, and inserting the segment into pBR322 at its EcoRI site. Recloning the EcoRI segment into M13mp7 in a useful location involved the filing-in of EcoRI ends of the globin segment so that it could be blunt-end ligated into mp7 DNA digested with Hinc II. Insertion at the Hinc II site assured that the insert could be effectively removed from single-stranded recombination phage DNA by EcoRI or Bam HI digestion.

Establishment of the orientation of the insert in clones, and determination of whether the insert strand in phage was coding or noncoding, was accomplished by restriction enzyme digestion, and hybridization of strand-specific synthetic probes to phage DNA.

EXAMPLE 8

The newly synthesized probe of Example 6 hybridizes with the 201 bp fragment of the Dde I digested nucleic acids containing β-globin gene. This probe is used for the detection of the digestion pattern in a sickle and normal β-globin genomic DNA following the procedure described in U.S. Pat. No. 4,395,486.

It will be understood that the specification and examples are illustrative but not limitative of the present invention and that other embodiments within the spirit and scope of the invention will suggest themselves to those skilled in the art.

What is claimed is:

1. A process for the production of a single strand of a nucleic acid, the processing comprising
    (a) tailing a 3' end of a nucleic acid with a terminal deoxynucleotidyl transferase and a ribonucleoside triphosphate,
    (b) oxidizing the product of step (a) to produce a nucleic acid with a pendant aldehyde group,
    (c) reacting the product the step (b) with a solid support, said solid support containing one or more NH$_2$ groups,
    (d) reacting the rpduct of step (c) with a primer nucleic acid to form a hybrid,
    (e) extending the primer on the hybrid with DNA polymerase and a nucleoside triphosphate,
    (f) denaturing the product of step (e), and
    (g) separating the product of step (f) into a soluble product and an insoluble product.

2. A process according to claim 1, wherein the insoluble product from step (g) is recycled to step (d) and steps (d), (e), (f) and (g) are conducted one or more times, each time the insoluble product of step (g) being recycled.

3. A process according to claim 1, wherein the ribonucleoside triphosphate in step (a) is ATP.

4. A process according to claim 1, wherein the nucleic acid in step (a) is DNA.

5. A process according to claim 1, wherein said solid support containing one or more NH$_2$ groups is prepared by reacting a solid support wit cyanogen bromide and a diamine.

6. A process according to claim 1, wherein the primer nucleic acid in stem (d) is an oligonucleotide.

7. A process according to claim 1, wherein the oxidizing in step (b) is conducted with periodate.

8. A process according to claim 1, wherein the nucleotide triphosphate in step (e) is selected from the group consisting of deoxy ATP, deoxy CTP, deoxy GTP, deoxy TTP and mixtures thereof.

9. A process according to claim 1, wherein the solid support is selected from the group consisting of cellulose, Sephadex, Sepharose, paper and nylon.

* * * * *